United States Patent [19]

Graudums et al.

[11] 4,399,145
[45] Aug. 16, 1983

[54] LACTAMS COMPOSITIONS AND PHARMACEUTICAL METHODS OF USE

[75] Inventors: Ivars Graudums; Elmar Friderichs, both of Stolberg, Fed. Rep. of Germany

[73] Assignee: Grunenthal GmbH, Stolberg, Fed. Rep. of Germany

[21] Appl. No.: 318,389

[22] Filed: Nov. 5, 1981

[30] Foreign Application Priority Data

Dec. 23, 1980 [DE]  Fed. Rep. of Germany ....... 3048663

[51] Int. Cl.³ .................. A61K 31/445; C07D 417/04
[52] U.S. Cl. ..................................... 424/267; 546/198
[58] Field of Search ......................... 546/198; 424/267

[56] References Cited

U.S. PATENT DOCUMENTS 3,951,985  9/1976  Graudums et al. ................ 546/198

*Primary Examiner*—Robert T. Bond
*Attorney, Agent, or Firm*—Weiser & Stapler

[57] ABSTRACT

The invention relates to new lactam compounds, pharmaceutical compositions containing them (especially those for oral or rectal application) and to processes for the preparation of these compounds and compositions. The new compounds have the general formula

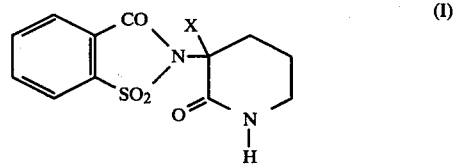

(I)

wherein X represents a straight or branched alkyl radical with 1 to 4 carbon atoms, preferably a methyl group. The new compounds of formula (I) have sedating-tranquilizing properties. In higher dosages some of them also act as hypno-anesthetics. Moreover the derivative in which X represents the methyl group has anticonvulsant activities. The valuable compounds of formula (I) are prepared in a manner known per se e.g. by reacting an 3-alkyl-3-halogen-2-oxopiperidine (the alkyl having 1–4 carbon atoms) with a metal derivative of 2,3-dihydro-3-oxo-1,2-benzisothiazoldioxid-(1,1) or by reacting an 3-alkyl-3-amino-2-oxopiperidine with o-sulfobenzoic acid dichloride or dibromide or with an o-halomercaptobenzoylhalide, followed by oxydation. Other processes known per se, such as cyclizations to form lactam rings, are also suitable for the preparation of the compounds of formula (I).

15 Claims, No Drawings

LACTAMS COMPOSITIONS AND PHARMACEUTICAL METHODS OF USE

The present invention relates to novel lactam compounds which show a broad range of the central nervous system moderating activities. The new compounds according to the invention have the general formula

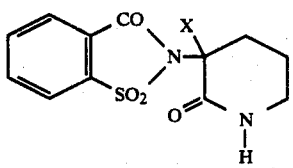

(I)

wherein X represents a straight or branched alkyl radical with 1 to 4 carbon atoms.

Preferably X is an alkyl radical having one or two carbon atoms and especially it represents the methyl group.

The compounds of formula I, especially the 3-(2,3-dihydro-1,1-dioxido-3-oxo-1,2-benzisothiazol-2-yl)-3-methyl-2-oxopiperidine (hereinafter referred to as "methyl derivative") have sedating-tranquilizing properties. In higher dosages the compounds of formula I, in which X represents a methyl or an ethyl radical, also act as hypno-anesthetics. It is especially remarkable that there is (contrary to the situation given for barbiturates and related compounds) a great difference between the dosages which have to be administered to produce said different effects. The compounds according to the invention also induce inhibition of gastro-intestinal secretion and motility. Furthermore the methyl derivative shows pronounced anticonvulsant activities.

While following the administration of barbiturates or of benzodiazepines several animal species and also certain human patients (for instance geriatric patients) may develop paradoxical excitations, such excitations are not produced by the compounds according to the invention.

Accordingly the compounds of the general formula I, especially the methyl derivative are indicated for therapy and prophylaxis of agitational states and restlessness, psychomostoric excitation, anxiety, sleep disturbances, cerebral seizures of the type of grand-mal- and petit-mal-epilepsy as well as of states hypermotility of the gastro-intestinal-tract (irritable stomach and irritable colon).

In these fields of indication the compounds are suitable for use in humans and animals.

The compounds of formula I are particularly suitable for oral or rectal application after incorporation in usual application forms.

Other objects of the invention accordingly are pharmaceutical compositions containing as active ingredients at least one or more of the compounds of formula I and the manufacture of such compositions. For oral application the compounds of formula I may be incorporated in solid compositions like tablets, pills, dragees, capsules and similar application forms, in the production of which generally used inorganic or organic adjuvants such as diluents, carriers, binders, lubricants and others are added. Such forms for oral administration can also be manufactured in a known manner so that release of the active ingredients is delayed in order to ensure that the patient is provided with active ingredients uniformly over a longer period of time.

Liquid compositions for oral application of the compounds of formula I are syrups, drops and the like, in the manufacture of which adjuvants may be used such as sugar-, invert sugar-, glucose solutions and so on.

Adjuvants to be used in the manufacture of suppositories are natural or hydrogenated or synthetic oils, waxes and so on.

Moreover suitable preservatives, stabilizers, wetting-, dissolving- and sweetening agents as well as coloring and aromatizing materials may be added. The pharmaceutical compositions of the invention are prepared in accordance with traditionally accepted standards.

The compositions contain per individual dose about 50 to 500 mg of the active ingredient. In time-released forms these amounts may be increased in relation to the rate of release.

The compounds of the invention are administered in dosages effective to cause the condition desired. In general the daily dose is 50 to 1000 mg/patient but due to the low toxicity of the compounds of formula I also higher total doses per day may be administered.

In the German Pat. No. 2 210 166 and related patents in other countries there are described compounds of the formula wherein R is a hydrogen atom or an alkyl group with 1 to 3 carbon atoms.

These compounds are effective as sedatives and hypnotics in men and animals but have no anesthetic activity (for instance in animal experiments the compounds of formula A, in which R is hydrogen, even on intraperitoneal administration of the extremely high dose of 10 000 mg/kg caused no anesthesia).

To the contrary, as mentioned above, the compounds of formula I in which X is a methyl or an ethyl group in higher dosages surprisingly also act as hypno-anesthetics. In animal experiments there were determined as values of the $ED_{50}$ (the dose, the administration of which causes the effect in 50% of the treated animals) for the "methyl derivative" with respect to the sedating activity 33.3 mg/kg (on intraperitoneal administration) or 258 mg/kg (on oral application), respectively, and with respect to the anesthetic activity the value of the $ED_{50}$ is 592 mg/kg on intraperitoneal administration.

In comparing the anticonvulsive activities of the compounds of formula A and those of the compound of formula I ($X=CH_3$) also an increase of this activity could be determined. For instance the compound A ($R=H$) shows activity only in the experimental convulsions induced by electro-shock ($ED_{50}$ 444 mg/kg on intraperitoneal administration), thus having the type of action of diphenylhydantoin. The "methyl derivative", however, is active not only in the convulsions induced by electro-shock ($ED_{50}$ 112 mg/kg intraperitoneally) but also in the same dosage range in the convulsions induced by pentylenetetrazole ($ED_{50}$ 91.4 mg/kg intraperitoneally) indicating that it additionally has the type of action of phenobarbital. It is of special interest, that for the known compound A ($R=H$) this activity in the convulsions induced by electro-shock only could observed after intraperitoneal but not after oral administration whereas for the "methyl derivative" according to the invention after oral application in this test an $ED_{50}$ value of 181 mg/kg was observed.

These valuable enlargements of the field of action which show the compounds of formula I and especially the methyl derivative in comparision to the known compounds of formula A are suprising and were unforeseeable.

Another object of the invention is the preparation of the new compounds of the general formula I. These compounds may be prepared by reacting a compound of formula II

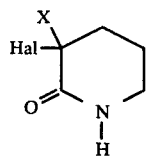
(II)

wherein X has the same meaning as above and wherein Hal represents an iodine atom or preferably a chlorine or bromine atom, with a compound of the general formula III

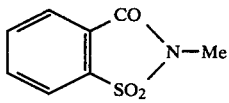
(III)

wherein Me indicates an alkali-metal, preferably sodium or potassium.

The reaction is generally carried out by dissolving the compound of general formula II in a suitable solvent and combining the resulting solution with a suspension or solution of the compound of general formula III, to which a small amount of sodium- or potassium iodide may have been added. Suitable reaction media include dimethyl formamide, dimethyl acetamide, dimethyl sulfoxide, aliphatic alcohols containing 1 to 8 carbon atoms, butyl acetate, acetonitril, open-chained or cyclic ethers like di-isopropyl ether, tetrahydrofuran or dioxane, toluene, xylene, cyclohexane, n-heptane and similar solvents or suspending agents. The reaction is preferably carried out at the boiling point of the medium used, although it can also be carried out over a correspondingly longer period at room temperature or with cooling. To work up the reaction solution water can be added to it or the reaction solution can be extracted with suitable organic solvents such as ethers, hydrocarbons or halogenated hydrocarbons and similar solvents. However, it is also possible to distill off the solvent used and to purify the remaining reaction product by washing with water and/or recrystallisation.

The compounds of general formula I can also be prepared by reacting a compound of general formula IV

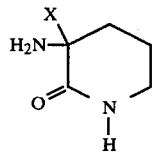
(IV)

in which X is as defined above or a salt of a compound of formula IV with o-sulfobenzoic acid dichloride or dibromide or with o-sulfobenzoic acid anhydride. Salts of the compounds of formula IV which may be used in this reaction are such as the hydrochlorides, hydrobromides, sulfates, phosphates, formiates, acetates, benzene sulfonates and similar salts with acids.

The reaction is best carried out in indifferent solvents, optionally with cooling and in the presence of acid-binding agents such as triethylamine, trimethylamine, diisopropylethylamine, sodium carbonate, potassium carbonate, sodium hydrogencarbonate or potassium hydrogencarbonate. The solvents used are—with the exception of the alcohols—the same as mentioned above for the reaction of the compounds of formulae II and III, there are preferably used as solvents in this case, however, dimethyl formamide, the ethers and the hydrocarbons mentioned above.

Starting with compounds of formula IV the compounds of formula I can also be prepared by reacting a compound of formula IV with a compound of formula

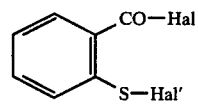
(V)

wherein Hal and Hal' have the same or a different meaning and each represents a bromine or iodine atom or preferably a chlorine atom in presence of a solvent or suspending agent and preferably in presence of a base at temperatures from about 0° to about 100° C. and then oxidizing the thus obtained compound of formula

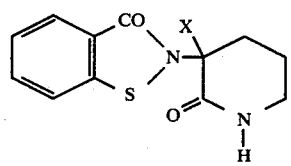
(VI)

wherein X has the same meaning as above in presence of an aliphatic carboxylic acid with 1 to 5 carbon atoms, serving as a solvent, at temperatures from about 25° to about 125° C. Suitable oxidizing agents are hydrogen peroxide or peroxy acids such as peroxyacetic acid, peroxypropionic acid, peroxybenzoic acid and others, there may also be used, however, other oxidizing agents such as potassium permanganate.

Bases to be used in the reaction of the compounds of formulae IV and V are preferably tertiary amines such as triethylamine, tripropylamine, N-ethylpiperidine or especially pyridine or a picoline which bases also may serve as solvents.

Some of the 3-amino-2-piperidones of formula IV are already known. They may easily be prepared by hydrogenating compounds of the formula

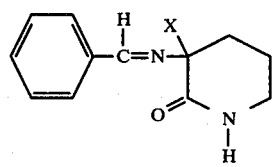

wherein X is a defined above in an indifferent solvent such as an alcohol and in presence of a noble metal catalyst, preferably palladium on charcoal. This hydrogenation may be made at about 20°-40° C. under normal pressure it is also possible, however, to use higher temperatures and/or higher pressures of hydrogen. To work up the catalyst is filtered off and the solution obtained is evaporated. Thus the compounds of formula IV are obtained in good yields generally with a purity sufficient so use them in the next step without intermediary purification.

The compounds of formula V are also already known. They may be prepared e.g. by halogenating diphenyldisulfide-2,2'-dicarboxylic acid dichloride or dibromide, especially by treating with chlorine or bromine in presence of a solvent such as dichloromethane, chloroform or carbon tetrachloride.

Furthermore the compounds of general formula I can be prepared by cyclization of a compound of formula VII

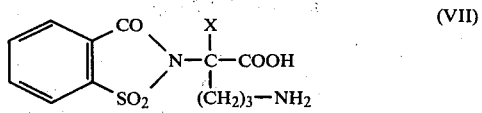

wherein X is as defined above by splitting off water. The ring closure can be achieved by using compounds such as phosphorus pentachloride, thionyl chloride, acetyl chloride, hydrogen chloride and similar acidic compounds able to facilitate splitting off water. However, it can also be produced solely by heating, optionally in presence of a high boiling solvent or suspending agent. It is also possible to use a functional derivative of the acid of general formula VII, for example an acid halide or an ester in which case the ring closure is made by splitting off the respective hydrogen halide or alcohol.

Another method of preparing compounds of general formula I is to cyclise a compound of general formula VIII

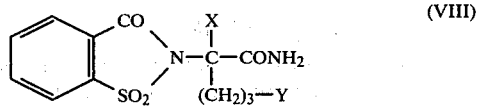

wherein X is as defined above whilst Y represents a chlorine, bromine or iodine atom or a hydroxy group by splitting off the compound of formula HY (which is hydrogen chloride, hydrogen bromide, hydrogen iodide or water, respectively). In case Y is chlorine, bromine or iodine this cyclization is made in the presence of inorganic or organic bases such as ammonia, aqueous potassium or sodium hydroxide solution, alkali alcoholates or amines like triethylamine. In this case, the amine can additionally serve as solvent, although such solvents as benzene, toluene or alcohols can also be used. The reaction takes place both at room temperatur and also at elevated temperature.

Represents, however, Y a hydroxy group, the cyclization is preferably made in presence of acidic dehydrating agents such as thionyl chloride, acetyl chloride and acetic anhydride. However, ring closure can also be produced solely by heating, optionally in presence of a high boiling solvent or suspending agent.

After the cyclization has been performed the reaction mixture is worked up in the same way as described above.

The compounds of general formula I contain an asymmetrically substituted carbon atom and, accordingly, can occur in optically active forms. The invention covers both the racemates and also the optically active forms of the compounds of general formula I and the methods by which they are produced. In the preparation of the optically active forms preferably optically active forms of the compounds of formulae II or IV, respectively, are reacted as described above with a compound of formula III or with o-sulfobenzoic acid dichloride or dibromide or with the compound of formula V, followed by oxydation, respectively. It is also possible, however, to use optically active forms of the compounds of formulae VII or VIII, respectively, or to split the racemic forms of the compounds of formula I in a manner known per se.

The following not limiting examples serve further to illustrate the invention. All temperature references are uncorrected. In carrying out the experiments on which the examples are based no importance was attached to obtain maximum yields.

EXAMPLE 1

6.8 g of 3-bromo-3-methyl-2-piperidone and 8 g of the dried sodium salt of 2,3-dihydro-3-oxo-1,2-benzisothiazol-1,1-dioxide are heated while stirring to 110°–115° in 25 ml of distilled dimethyl formamide for a period of 75 minutes. After cooling 75 ml of water are added and the stirring is continued for further 30 minutes. The precipitate is filtered off, washed with water, dried in a vacuum at 80° C. and then recrystallized from n-butanol. 3-(2,3-Dihydro-1,1-dioxido-3-oxo-1,2-benzisothiazol-2-yl)-3-methyl-2-oxo-piperidine melting at 211° to 215° C. is thus obtained in a yield of 24% of the theoretical.

The 3-bromo-3-methyl-2-piperidone used above as starting material is obtained as follows:

A mixture of 5.15 g of 3-methyl-2-piperidone (Ber. 24 page 2445) and 50 ml of chloroform is chilled to about 0° C. Then there are added while stirring at 0°–5° C. 19 g of phosphorus pentachloride, followed by 0.2 g of anhydrous zinc chloride. The mixture is heated to about 15° C., treated dropwise with a solution of 2.5 ml of bromine in 5 ml of chloroform and then heated to 40° C. for 5 hours, while stirring. After cooling the mixture is poured on ice and treated with sodium hydrogensulfite until it is discolored. The layers are separated and the aqueous phase is extracted with chloroform. The combined chloroform layers are dried over magnesium sulfate and then the solvent is distilled off in vacuo. The semi-solid residue is recrystallized from acetone to give 3-bromo-3-methyl-2-piperidone melting at 107° to 109° C. in a yield of 81% of the theoretical.

EXAMPLE 2

6.3 g of 3-amino-3-methyl-2-piperidone [J.Med.-Chem. 21, 50–55 (1978)] are dissolved in 46 ml of absolute dimethyl formamide. While cooling with ice 11.8 g of o-sulfo benzoic acid dichloride melting at 79° C. (Beistein Vol. 11, 374) are added followed by the dropwise addition at about 0° C. of 13.9 ml of triethylamine to the reaction mixture. The mixture is then stirred for 24 hours at 0° C., treated while cooling with ice with 120 ml of distilled water and thereafter extracted with chloroform. The chloroform extracts are washed with water, dried over magnesium sulfate and then the solvent is distilled off in vacuo. The residue is dissolved in a small amount of hot absolute ethanol, stirred in an ice bath to give crystals which are filtered off and recrystalized from n-butanol. 3-(2,3-Dihydro-1,1-dioxido-3-oxo-1,2-benzisothiazol-2-yl)-3-methyl-2-oxo-piperidine is thus obtained in the form of white crystals melting at 211° to 215° C. and being identical with the product obtained in example 1. The yield is 64% of the theoretical.

EXAMPLE 3

2.05 g of 3-amino-3-ethyl-2-piperidone are dissolved in 15 ml of absolute dimethyl formamide. While cooling with ice 3.45 g of o-sulfo benzoic acid dichloride are added followed by the dropwise addition at 0°–5° C. of 4.05 ml of triethylamine to the reaction mixture. The mixture is then left to react for a time while cooling with ice, subsequently held at room temperature for some hours whereafter 45 ml of distilled water are added. The mixture is extracted with chloroform, the chloroform extracts are washed with water, dried over magnesium sulfate and then the chloroform is distilled off in vacuo. The residue is dissolved in hot ethyl acetate. After cooling the crystals formed are filtered off and recrystallized from n-butanol. Thus 3-(2,3-dihydro-1,1-dioxido-3-oxo-1,2-benzoisothiazol-2-yl)-3-ethyl-2-oxo-piperidine is obtained in a yield of 45% of the theoretical in the form of white crystals melting at 207° to 209° C.

The 3-amino-3-ethyl-2-piperidone used above as starting material is obtained as follows:

3.3 g of 3-benzalimino-3-ethyl-2-piperidone [J.Med.-Chem. 18, 600 (1975)] are dissolved in 200 ml of absolute ethanol. 5 g of 10% palladium on charcoal are added and then the compound is hydrogenated at room temperature and atmospheric pressure, until the calculated amount of hydrogen has been consumed. The catalyst is filtered off and the filtrate is evaporated under low pressure. The residue is dried in vacuo at 50° C. Thus the 3-amino-3-ethyl-2-piperidone is obtained in a yield of 95% of the theoretical in sufficiently pure form for further reaction.

EXAMPLE 4

A solution of 5 g of 5-amino-2-(2,3-dihydro-1,1-dioxido-3-oxo-1,2-benzisothiazol-2-yl)-2-methyl-pentanoic acid in 150 ml of toluene is boiled under reflux, using a water separator, until the separation of water stops. The mixture is cooled, concentrated in vacuo to a small volume and the precipitate is filtered off, recrystallization from n-butanol gives 3-[2,3-dihydro-1,1-dioxide-3-oxo-1,2-benzisothiazol-2-yl]-3-methyl-2-oxo-piperidine melting at 211° to 215° C., identical with the product obtained in example 1. The yield is 31% of the theoretical

EXAMPLE 5

3.75 g of 5-bromo-2-(2,3-dihydro-1,1-dioxido-3-oxo-1,2-benzisothiazol-2-yl)-2-methyl-valeramid are dissolved in 100 ml of xylene. After adding 1.3 g of ethyl diisopropylamine the solution is heated for 2 hours to reflux temperature. After cooling and concentration in vacuo to a small volume, the product is filtered. The residue is recrystallized from n-butanol. 3-(2,3-Dihydro-1,1-dioxido-3-oxo-1,2-benzisothiazol-2-yl)-3-methyl-oxopiperidine, melting at 211° to 215° C. identical with the product obtained in example 1 is obtained.

Yield: 25% of the theoretical.

EXAMPLE 6

5 g 2-(2,3-Dihydro-1,1-dioxido-3-oxo-1,2-benzisothiazol-2-yl)-5-hydroxy-2-methyl-valeramid are dissolved in 150 ml of xylene and the resulting solution is boiled under reflux for several hours, using a water separator. After the theoretical quantity of water has been separated off, the mixture is allowed to cool and concentrated in vacuo to a small volume. The precipitate is filtered off and recrystallized from n-butanol to give 3-(2,3-dihydro-1,1-dioxido-3-oxo-1,2-benzisothiazol-2-yl)-3-methyl-2-oxo-piperidine in the form of white crystals melting at 211° to 215° C., identical with the product obtained in example 1. The yield is 37% of the theoretical.

EXAMPLE 7

The procedure is the same as in example 2, there are used, however, instead of the 3-amino-3-methyl-2-piperidone 7.7 g of 3-amino-3-n-propyl-2-piperidone or 8.4 g of 3-amino-3-n-butyl-2-piperidone, respectively, to give
3-(2,3-dihydro-1,1-dioxido-3-oxo-1,2-benzisothiazol-2-yl)-3-n-propyl-2-oxo-piperidine melting at 235° to 237° C. in a yield of 26% of the theoretical and, respectively,
3-n-butyl-3-(2,3-dihydro-1,1-dioxido-3-oxo-1,2-benzisothiazol-2-yl)-2-oxo-piperidine melting at 220° to 222° C. in a yield of 21% of the theoretical.

EXAMPLE 8

11.8 g of o-sulfobenzoic acid dichloride are dissolved in 50 ml of absolute tetrahydrofuran. While cooling with ice and stirring at 0° C. a solution of 6.3 g of 3-amino-3-methyl-2-piperidone and of 13.9 ml of triethylamine in 30 ml of absolute dimethylformamide is added dropwise. The mixture is stirred for 24 hours at about 0° C. and then while cooling treated with 250 ml of water. The precipitate is filtered off, washed with water and recrystallized from n-butanol to give the same product as obtained in example 1, melting at 211°–215° C., in a yield of 68% of the theoretical.

EXAMPLE 9

25.6 g of 3-amino-3-methyl-2-piperidone are added at −20° to 300 ml of absolute dimethylformamide. While stirring 47.8 g of o-sulfobenzoic acid dichloride are added followed after 15 minutes by 55.2 ml of triethylamine which is dropwise added whereby the temperature is maintained at about −18° C. to −20° C. The mixture is stirred for 45 hours at about −20° C. and then, while cooling, 400 ml of water are added in such a rate that the temperature remains below 0° C. 200 ml of chloroform are added and then the temperature is allowed to raise to about 18° C.

The precipitate is filtered off, washed with water, dried and finally recrystallized from methanol to give 3-(2,3-dihydro-1,1-dioxido-3-oxo-1,2-benzisothiazol-2-yl)-3-methyl-2-oxopiperidine in the form of white crystals melting at 211° to 215° C. Yield 65% of the theoretical.

EXAMPLE 10

4.3 g of 3-amino-3-methyl-2-piperidone are dissolved in 25 ml of pyridine. While stirring a solution of 6.9 g of 2-chloromercaptobenzoylchloride in 25 ml of carbon tetrachloride is added slowly, followed by the addition of 25 ml carbon tetrachloride. The stirred mixture is heated to about 60° C. for 30 minutes, cooled and treated with ice water. The layers are separated and the aqueous layer is extracted with carbon tetrachloride. The combined organic layers are washed with water, dried with magnesium sulfate and then evaporated in vacuo. The residue is dissolved in 25 ml of glacial acetic acid and, while stirring, 10 ml of a 50% solution of peroxy acetic acid are added slowly. The stirred mixture is heated slowly to about 100° C. and after 30 minutes at this temperature it is cooled to room temperature. There are added slowly 5 ml of methanol followed after 10 to 15 minutes by 200 ml of water. The precipitate is filtered off, washed with water and recrystallized from n-butanol. 3-(2,3-Dihydro-1,1-dioxido-3-oxo-1,2-benzisothiazol-2-yl)-3-methyl-2-oxopiperidine melting at 211°-215° C. is thus obtained in a yield of 21% of the theoretical.

The valuable biological properties of the compounds of formula I, especially those of the "methyl derivative" described herein above were determined by using inter alia the following tests:

After administration of the test compounds single male mice were put into small cages and the movements of the cages were continuously recorded over a period of one hour. The intensity and number of movements of the treated animals were compared with that of untreated controls. The amount of a test compound necessary to cause a 50% reduction of the movements is the "$ED_{50}$" with respect to the sedative activity of the compound. As mentioned already above the $ED_{50}$ values for the methyl derivative are 33,3 mg/kg (after intraperitoneal administration) and 258 mg/kg (oral application), respectively. [The $ED_{50}$ values for compound A (R=H) are 34,4 mg/kg (intraperitoneally) and 156 mg/kg (orally), respectively, and for phenobarbital the $ED_{50}$ is about 50 mg/kg (intraperitoneally) in this test].

For the determination of their hypno-anesthetic effects the test compounds were administered to mice intraperitoneally. 60 minutes after the application the mice were brought into lateral position. If they maintain for more than 30 seconds in that position the righting reflex is deemed to be abolished indicating an anesthetic effect. In this way for the methyl derivative there was determined an $ED_{50}$ value of 592 mg/kg for the hypno-anesthetic activity whereas for the compound of formula A (R=H) no anesthetic effect was observed even after intraperitoneal application of 10 000 mg/kg. On the other side for phenobarbital the anesthetic $ED_{50}$ was determined to 106 mg/kg (intraperitoneally) i.e. about only twice the amount of the $ED_{50}$ determined in the test for sedative activity.

In the test for anticonvulsant activity male mice were treated 60 minutes after oral or 30 minutes after intraperitoneal application of the test compounds with a current impulse (50 Hz; 20 mA) of 0,2 sec duration using corneal electrodes. This causes in untreated animals tonic convulsions of the hind legs which may be—dependend from the dose applied-prevented by anticonvulsant compounds as for instance the "methyl derivative" of the invention the $ED_{50}$ values of which are 112 mg/kg on intraperitoneal application and 181 mg/kg on oral administration. In testing the compound A (R=H) an $ED_{50}$ value of 444 mg/kg (intraperitoneally) could be determined whereas on oral application of this compound no anticonvulsant action could be observed.

Administration of 85 mg/kg pentylenetetrazole subcutaneously to male mice causes clonic (and tonic) convulsions in the animals. Depending from the amount applied intraperitoneally 45 minutes before the treatment with pentylenetetrazole the methyl derivative may prevent such convulsions, the $ED_{50}$ being 91,4 mg/kg. To the contrary the compound of formula A (R=H) up to an amount of 1000 mg/kg (applied intraperitoneally) was ineffective in preventing the convulsions.

To test the effect of the compounds on gastro-intestinal motility rats were administered intragastrally on empty stomages 3 ml=3,1 g of a food suspension. 2 hours later the animals were killed, the stomages were collected and the amounts of food remaining in the stomages determined. If the animals were treated with the test compounds (intraperitoneal application) 30 minutes before the administration of the food suspension a retardation of the food passage dependend on the applied amount of the test compound could be observed. For the methyl derivative the dose which causes the duplication of the amount of food remaining in the stomages in comparison to the values found in untreated animals is 42,6 mg/kg.

What we claim is:

1. A compound of the formula I

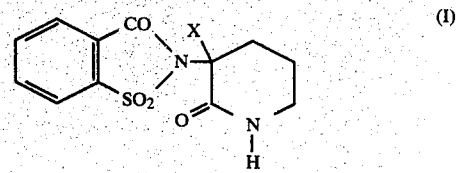

wherein X represents a straight or branched alkyl radical with 1 to 4 carbon atoms.

2. The compound of claim 1 wherein X is an alkyl radical with one or two carbon atoms.

3. The compound of claim 1 which is 3-(2,3-dihydro-1,1-dioxido-3-oxo-1,2-benzisothiazol-2-yl)-3-methyl-2-oxopiperidine having the formula

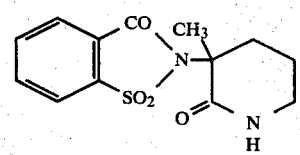

4. The compound of claims 1, 2 or 3 which comprise the optically active form of said compound.

5. A pharmaceutical sedating-tranquilizing, hypno-anesthetic and anticonvulsant composition comprising a biologically acceptable carrier and a therapeutically effective amount of a compound of any one of claims 1, 2, or 3.

6. The composition of claim 5 wherein the compound is present in an optically active form.

7. The composition of claim 5 wherein the compound is present in an amount of from about 50 to about 500 mg per single dosage form.

8. The composition of claims 5 or 6 wherein the composition is in a suitable form for oral administration.

9. The composition of claim 8 wherein the composition is in a form for retarded release of the active ingredients.

10. An anticonvulsant composition comprising a biologically acceptable carrier and an effective anticonvulsant amount of 3-(2,3-dihydro-1,1-dioxido-3-oxo-1,2-benzisothiazol-2-yl)-3-methyl-2-oxopiperidine.

11. A hypno-anesthetic composition comprising a biologically acceptable carrier and an effective hypno-anesthetic amount of 3-(2,3-dihydro-3-oxo-1,2-benzisothiazol-2-yl)-3-methyl-2-oxopiperidine.

12. A method of treating a patient suffering from epilepsy which comprises administering to said patient an effective amount of a composition comprising a biologically acceptable carrier and a compound of claims 1, 2 or 3.

13. A method of therapeutically or prophylactically treating a patient for convulsions which comprises administering to said patient an effective amount of a composition according to claim 10.

14. A method of sedating a patient in need of sedation comprising administering to said patient an effective amount of a composition comprising a suitable biologically acceptable carrier and a compound of claims 1, 2 or 3.

15. The method of claim 14 wherein the composition is administered orally.

* * * * *